US00PP33364P3

(12) United States Plant Patent
Schoemaker

(10) Patent No.: US PP33,364 P3
(45) Date of Patent: Aug. 17, 2021

(54) ***HYDRANGEA* PLANT NAMED 'LC NO6'**

(50) Latin Name: *Hydrangea paniculata*
Varietal Denomination: LC NO6

(71) Applicant: Alex Frederick Schoemaker, Boskoop (NL)

(72) Inventor: Alex Frederick Schoemaker, Boskoop (NL)

(73) Assignee: Alex Schoemaker Creations Holding B.V., Boskoop (NL)

( * ) Notice: Subject to any disclaimer, the term of this patent is extended or adjusted under 35 U.S.C. 154(b) by 0 days.

(21) Appl. No.: 16/974,062

(22) Filed: Sep. 18, 2020

(65) Prior Publication Data

US 2021/0120716 P1 Apr. 22, 2021

Related U.S. Application Data

(60) Provisional application No. 62/973,658, filed on Oct. 17, 2019.

(51) Int. Cl.
*A01H 5/00* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./226, 250
See application file for complete search history.

(56) References Cited

PUBLICATIONS

Polish Nurserymen Association website. 2020. https://zszp.pl/en/plant-novelties-competition-2020/hydrangea-paniculata-living-royal-flower-lc-no6-pbr/. Retrieved from the internet Dec. 8, 2020. 3 pages. (Year: 2020).*

* cited by examiner

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Hydrangea* plant named 'LC NO6', characterized by its upright to somewhat outwardly spreading and uniform plant habit; freely branching habit with strong lateral branches; early and freely flowering habit with plants remaining in flower for a long period time; dense and hardy inflorescences with large white-colored sterile flowers; and good garden performance.

2 Drawing Sheets

Botanical designation: *Hydrangea paniculata.*
Cultivar denomination: 'LC NO6'.

CROSS-REFERENCED TO CLOSELY RELATED APPLICATIONS

Title: Varieties of *Hydrangea* Plants
Inventor/Applicant: Alex Frederick Schoemaker
Provisional application Ser. No. 62/973,658
Filed: Oct. 17, 2019
Inventor/Applicant hereby claim the benefit of this provisional U.S. Patent Application.

STATEMENT REGARDING PRIOR DISCLOSURES BY INVENTOR/APPLICANT

An European Community Plant Breeder's Rights application for the instant plant was filed by the Inventor/Assignee, Mr. Alex Frederick Schoemaker of Boskoop, The Netherlands on Oct. 19, 2018, application number 2018/2636. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO6'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from an open-pollination in July, 2014 in Boskoop, The Netherlands, of *Hydrangea paniculata* 'DVP Pinky', disclosed in U.S. Plant Pat. No. 16,166, as the female, or seed, parent with an unknown proprietary selection of *Hydrangea paniculata* as the male, or pollen, parent. The new *Hydrangea* plant was discovered and selected by the Inventor as a single flowering plant from within the progeny of the stated open-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO6'. These characteristics in combination distinguish 'LC NO6' as a new and distinct *Hydrangea* plant:

1. Upright to somewhat outwardly spreading and uniform plant habit.
2. Freely branching habit with strong lateral branches.
3. Early and freely flowering habit with plants remaining in flower for a long period time.
4. Dense and hardy inflorescences with large white-colored sterile flowers.
5. Good garden performance.

Plants of the new *Hydrangea* can be compared to plants of the female parent, 'DVP Pinky'. Plants of the new *Hydrangea* differ primarily from plants of 'DVP Pinky' in the following characteristics:

1. Plants of the new *Hydrangea* have larger inflorescences than plants of 'DVP Pinky'.
2. Inflorescences of plants of the new *Hydrangea* are distally more rounded than and not as pointed as inflorescences of plants of 'DVP Pinky'.

Plants of the new *Hydrangea* can be compared to plants of the *Hydrangea paniculata* 'Phantom', not patented. In side-by-side comparisons, plants of the new *Hydrangea* differ primarily from plants of 'Phantom' in the following characteristics:

1. Plants of the new *Hydrangea* are more compact than plants of 'Phantom'.
2. Plants of the new *Hydrangea* have larger inflorescences than plants of 'Phantom'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'LC NO6' grown in a container.

The photographs on the second sheet are close-up views of a typical leaf (top of sheet) and typical inflorescences (bottom of sheet) of 'LC NO6'.

DETAILED BOTANICAL DESCRIPTION

Plants used in the aforementioned photographs and in the following description were grown during the late summer in 15-cm containers in an outdoor nursery in Boskoop, The Netherlands and under cultural practices typical of commercial *Hydrangea* production. During the production of the plants, day temperatures ranged from about 16° C. to 35° C. and night temperatures ranged from about 12° C. to 22° C. Plants of the new *Hydrangea* were pinched one time and were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO6'.

Parentage:

*Female, or seed, parent.*—*Hydrangea paniculata* 'DVP Pinky', disclosed in U.S. Plant Pat. No. 16,166.

*Male, or pollen, parent.*—Unknown proprietary selection of *Hydrangea paniculata*, not patented.

Propagation:

*Type cutting.*—By vegetative tip cuttings.

*Time to initiate roots, summer.*—About 16 days at temperatures about 16° C. to 30° C.

*Time to produce a rooted young plant, summer.*—About 120 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright to somewhat outwardly spreading and uniform plant habit; overall plant shape, upright narrowly obovate to oblong; strong and sturdy stems; moderately vigorous to vigorous growth habit and moderate to high growth rate.

*Plant height.*—About 80.3 cm.

*Plant diameter or area of spread.*—About 37.9 cm.

Lateral branch description:

*Branching habit.*—About eight lateral branches develop per plant; pinching enhances lateral branch development.

*Length.*—About 56.4 cm.

*Diameter.*—About 5 mm.

*Internode length.*—About 7.3 cm.

*Texture.*—When developing, sparsely pubescent; fully developed, woody.

*Aspect.*—Upright to about 15° from vertical.

*Strength.*—Strong, sturdy.

*Color.*—When developing: Close to 185A. Developed: Close to 200D; when woody, close to 199C and 200C.

*Lenticels.*—Density: Sparsely; none observed on developing stems. Size, developed stems: About 1 mm by 0.5 mm. Color, developed stems: Close to 174D.

Leaf description:

*Arrangement.*—Opposite, simple.

*Length.*—About 11.7 cm.

*Width.*—About 5.5 cm.

*Shape.*—Ovate to narrowly ovate.

*Apex.*—Acuminate to apiculate.

*Base*.—Obtuse to short attenuate.

*Margin*.—Serrate.

*Texture, upper and lower surfaces*.—Moderately pubescent; slightly rough; slightly rugose.

Venation pattern: Pinnate.

*Color*.—Developing leaves, upper surface: Close to 144A. Developing leaves, lower surface: Close to 144B. Fully developed leaves, upper surface: Close to between 143B and 144A; venation, close to 152B. Fully developed leaves, lower surface: Close to between 146C and 147C; venation, close to 196B, proximally, tinged with close to 180D.

*Petioles*.—Length: About 2.6 cm. Diameter: About 2 mm. Texture and luster, upper surface: Mostly smooth and glabrous, margins moderately pubescent; matte. Texture and luster, lower surface: Sparsely pubescent; matte. Color, upper surface: Close to 152D; towards the edges, close to 180A. Color, lower surface: Close to 177D; towards the edges, close to 180A.

Flower description:

*Flower type and habit*.—Showy sterile flowers and smaller inconspicuous fertile flowers arranged on terminal panicles; panicles dense and broadly conical in shape; sterile flowers face upright to outwardly and slightly drooping depending on their position in the inflorescence; fertile flowers face mostly upright.

*Fragrance*.—Faintly fragrant; sweet and pleasant.

*Natural flowering season*.—Flowering begins in the midsummer and is continuous until late summer in Northern Europe.

*Flower longevity*.—Sterile flowers last about six weeks on the plant, sterile flowers persistent; fertile flowers last about five days on the plant, fertile flowers not persistent.

*Quantity of flowers*.—Freely flowering habit; about 600 sterile flowers and about 300 fertile flowers per panicle.

*Panicle height*.—About 22.3 cm.

*Panicle diameter*.—About 19.9 cm.

*Sterile flower buds*.—Length: About 8 mm. Diameter: About 9 mm. Shape: Cup-shaped. Color: Close to 150D.

*Fertile flower buds*.—Length: About 4 mm. Diameter: About 3 mm. Shape: Obovate. Color: Close to 157C; distally, tinged with close to 63D; immature calyx, close to 157C.

*Sterile flower diameter*.—About 2.5 cm to 4.2 cm.

*Sterile flower depth* (*height*).—About 5 mm.

*Fertile flower diameter*.—About 9 mm.

*Fertile flower depth* (*height*).—About 6 mm.

*Petals, sterile flowers*.—Quantity and arrangement: Four arranged in a single whorl. Length: About 3 mm. Width: About 1.25 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155D; apex slightly tinged with close to 63D; color does not change with development.

*Petals, fertile flowers*.—Quantity and arrangement: Five arranged in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155B; color does not change with development.

*Sepals, sterile flowers*.—Quantity and arrangement: Typically four or occasionally five arranged in a single whorl. Length: About 1.7 cm. Width: About 9 mm. Shape: Obovate to elliptic. Apex: Obtuse to broadly and bluntly acute. Base: Cuneate. Margin: Entire. Texture and luster, upper and lower surfaces: Smooth, glabrous; matte. Color: When opening and fully opened, upper surface: Close to 155A; with subsequent development (at the end of summer and beginning of autumn), color becoming closer to 186A to 186B. When opening and fully opened, lower surface: Close to 155C; with subsequent development (at the end of summer and beginning of autumn), color becoming closer to 186C.

*Sepals, fertile flowers*.—Quantity and arrangement: Five in a single whorl. Length: About 1.2 mm. Width: About 1.2 mm. Shape: Deltoid. Apex: Broadly acuminate. Base: Broadly cuneate. Margin: Entire. Texture and luster, upper and lower surfaces: Smooth, glabrous; matte. Color: When opening, upper and lower surfaces: Close to 157B. Fully opened, upper and lower surfaces: Close to 157B; color does not change with development.

*Pedicels, sterile flowers*.—Length: About 2.6 cm. Diameter: About 0.8 mm. Strength: Moderately strong. Aspect: About 75° from branch axis. Texture and luster: Moderately pubescent; matte. Color: Close to 155C.

*Pedicels, fertile flowers*.—Length: About 3 mm. Diameter: About 0.5 mm. Strength: Moderately strong. Aspect: About 20° from vertical. Texture and luster: Densely pubescent; matte. Color: Close to 155C.

*Reproductive organs, sterile flowers*.—Stamens: Quantity per flower: About 15. Filament length: About 2.5 mm. Filament color: Close to NN155B. Anther length: About 0.5 mm. Anther shape: Broadly oblong. Anther color: Close to 155A. Pollen amount: Moderate. Pollen color: Close to 156A. Pistils: To date, pistil development has not been observed on sterile flowers of plants of the new *Hydrangea*.

*Reproductive organs, fertile flowers*.—Stamens: Quantity per flower: About ten. Filament length: About 5 mm. Filament color: Close to NN155D. Anther length: About 0.5 mm. Anther shape: Broadly oblong. Anther color: Close to 155A. Pollen amount: Moderate. Pollen color: Close to 156A. Pistils: Pistil quantity per flower: Typically three or occasionally two. Pistil length: About 1 mm. Stigma shape: Club-shaped. Stigma color: Close to 157D. Style length: About 0.5 mm. Style color: Close to 157D. Ovary color: Close to 157A.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO6' as illustrated and described.

* * * * *

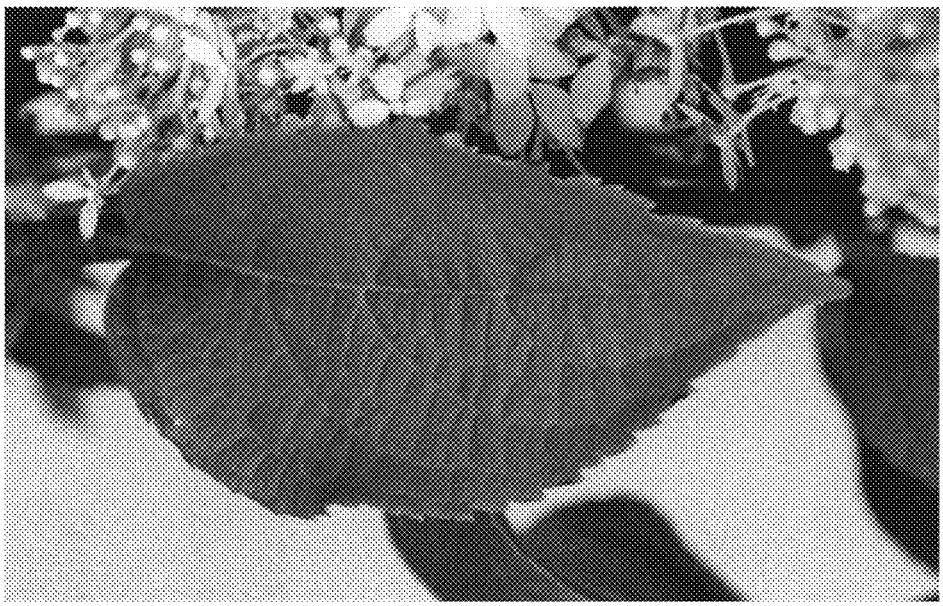
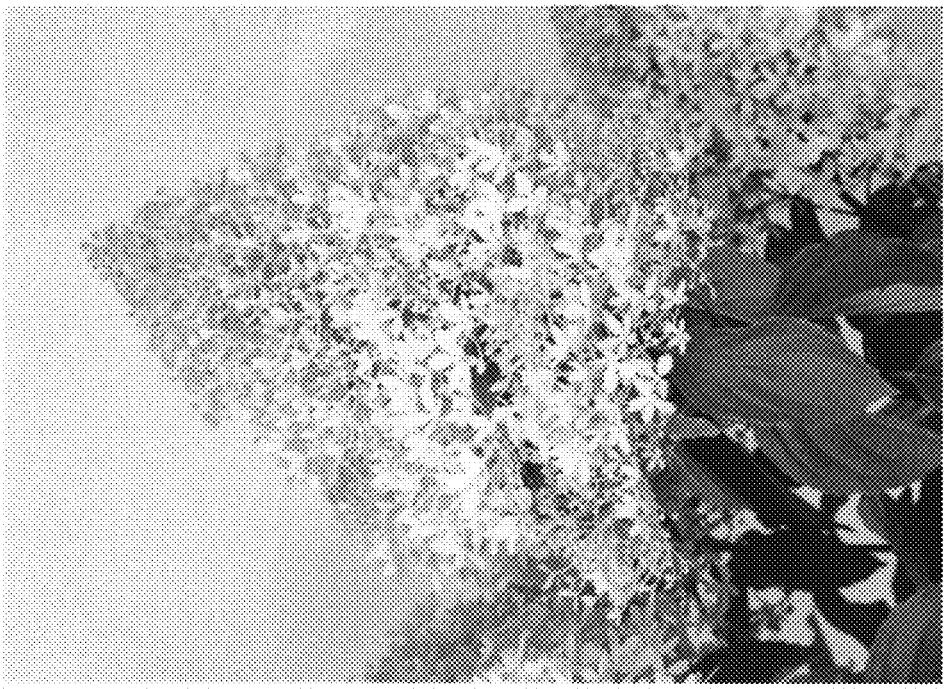

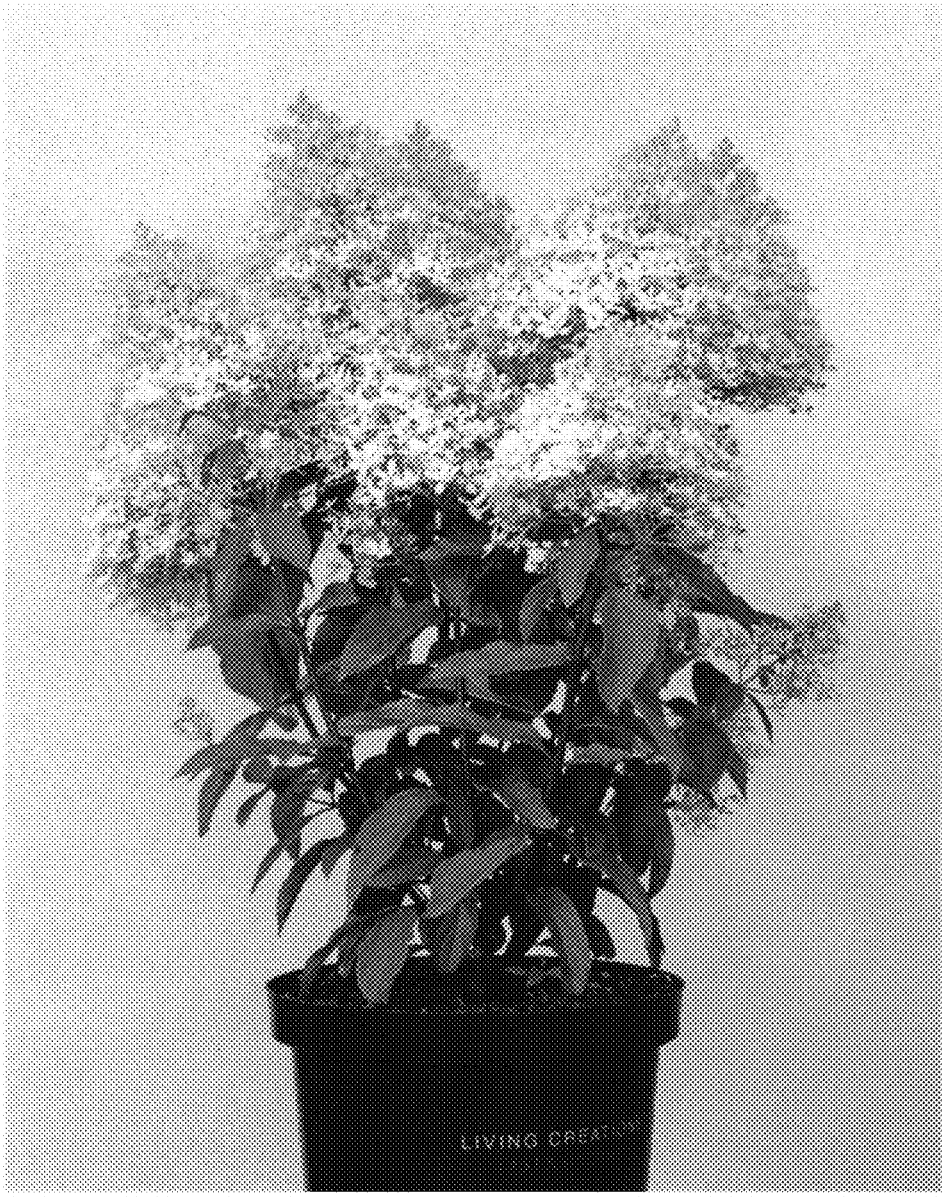
LIVING